US009770206B2

(12) United States Patent
Ashokan

(10) Patent No.: US 9,770,206 B2
(45) Date of Patent: Sep. 26, 2017

(54) TOUCH INPUT BIOMETRIC APPARATUSES AND METHODS OF USING THE SAME

(71) Applicant: Rajeev Ashokan, Hackensack, NJ (US)

(72) Inventor: Rajeev Ashokan, Hackensack, NJ (US)

( * ) Notice: Subject to any disclaimer, the term of this patent is extended or adjusted under 35 U.S.C. 154(b) by 427 days.

(21) Appl. No.: 14/568,874

(22) Filed: Dec. 12, 2014

(65) Prior Publication Data

US 2015/0201884 A1 Jul. 23, 2015

Related U.S. Application Data

(60) Provisional application No. 61/928,658, filed on Jan. 17, 2014.

(51) Int. Cl.

| G01G 19/50 | (2006.01) |
|---|---|
| A61B 5/00 | (2006.01) |
| G01G 23/37 | (2006.01) |
| A61B 5/053 | (2006.01) |

(52) U.S. Cl.
CPC .......... *A61B 5/4872* (2013.01); *A61B 5/0537* (2013.01); *A61B 5/6898* (2013.01); *G01G 19/50* (2013.01); *G01G 23/37* (2013.01)

(58) Field of Classification Search
CPC ...... G01G 19/50; G01G 23/37; A61B 5/4872; A61B 5/0537; A61B 5/6898
See application file for complete search history.

(56) References Cited

U.S. PATENT DOCUMENTS

| 4,893,685 A * | 1/1990 | Bergman | G01G 19/44 |
| | | | 116/DIG. 32 |
| 6,487,445 B1 * | 11/2002 | Serita | A61B 5/0537 |
| | | | 600/547 |
| 6,532,385 B2 * | 3/2003 | Serizawa | A61B 5/0537 |
| | | | 600/547 |
| 6,844,506 B2 * | 1/2005 | Nuesch | G01G 23/01 |
| | | | 177/25.11 |
| 6,920,352 B2 * | 7/2005 | Shimomura | A61B 5/0537 |
| | | | 600/547 |
| 7,009,119 B2 | 3/2006 | Carlucci et al. | |
| 7,104,954 B2 * | 9/2006 | Koyama | A61B 5/0537 |
| | | | 600/300 |
| 7,557,311 B2 * | 7/2009 | Umemoto | A61B 5/0537 |
| | | | 177/25.16 |
| 8,265,901 B2 * | 9/2012 | Petrucelli | A61B 5/022 |
| | | | 702/104 |

(Continued)

*Primary Examiner* — Randy Gibson
(74) *Attorney, Agent, or Firm* — Patentfile, LLC; Bradley C. Fach; Steven R. Kick

(57) ABSTRACT

A touch input biometric apparatus for measuring and communicating biometric data of a user which in preferred embodiments may comprise a platform configured to receive the weight of a user; a touch screen display integrated into the top surface of the platform and configured to receive touch input from a user; a first and a second BIA measurement zone comprising an electrically conductive material integrated into the top surface of the platform and configured to transfer an electrical current through the body of a user, said electrically conductive material electrically coupled to a BIA sensor configured to measure electrical impedance; and a weight sensor configured to measure the weight of the user on the platform. The apparatus may display the user's weight, estimation of percent body fat, or other biometric data on the touch screen display.

15 Claims, 13 Drawing Sheets

(56) References Cited

U.S. PATENT DOCUMENTS

| | | | |
|---|---|---|---|
| 8,475,367 B1 | 7/2013 | Yuen et al. | |
| 8,822,847 B2 | 9/2014 | Vidal et al. | |
| 9,498,137 B2 * | 11/2016 | Baker | A61B 5/0205 |
| 2004/0003947 A1 | 1/2004 | Kesselman et al. | |
| 2010/0004096 A1 * | 1/2010 | Inoue | A61B 5/053 |
| | | | 482/8 |
| 2011/0240379 A1 * | 10/2011 | Forshaw | G01G 19/44 |
| | | | 177/1 |
| 2012/0222903 A1 | 9/2012 | King et al. | |
| 2013/0289889 A1 * | 10/2013 | Yuen | G06F 19/3418 |
| | | | 702/19 |
| 2013/0341104 A1 | 12/2013 | Suzuki | |
| 2014/0083779 A1 | 3/2014 | Sharma | |
| 2015/0359441 A1 * | 12/2015 | Giovangrandi | A61B 5/0295 |
| | | | 600/509 |
| 2015/0362360 A1 * | 12/2015 | Kovacs | G01G 19/44 |
| | | | 177/245 |
| 2017/0042430 A1 * | 2/2017 | Kovacs | A61B 5/0205 |

\* cited by examiner

TOUCH INPUT BIOMETRIC APPARATUSES AND METHODS OF USING THE SAME

CROSS REFERENCE TO RELATED APPLICATIONS

This application claims priority to and the benefit of the filing date of U.S. Provisional Application No. 61/928,658, filed on Jan. 17, 2014, entitled "MULTI-TOUCH SCREEN FITNESS SCALE", which is hereby incorporated by reference in its entirety.

FIELD OF THE INVENTION

The present patent specification relates to electronic devices. More particularly, the present patent specification relates to touch screen input devices designed to enable one or more users to track and record biometrics such as body fat and weight.

BACKGROUND

Weighing scales in use today typically have a small LCD panel on the body of the scale which is used to display an individual's weight and other body metric data and may also have one or more buttons or other inputs to change the data that may be displayed on the LCD panel. These scales sometimes have electrodes on the body of the scale that when in contact with the user's skin, may provide body composition data which may also be displayed on the LCD panel. Body composition data may include a biometric analysis which is used to estimate the percentage of body fat and may be undertaken by passing a small current from one side of the body and measuring it as it exits from the other side. This analysis, also called as Bio-Impedance Electrical Analysis (BIA) is available in numerous bathroom scales today.

With the advent of touch screen electronic devices, many devices today are converging towards tactile input or touch screen technology. However, a weighing scale with touch screen technology that is able to perform a BIA is not available today. A primary reason why a combination of BIA technology and touch screen technology does not exist today is because touch screen technology typically works by detecting disturbances in the electrical field around the screen when the screen is touched by a user, while BIA technology works when a user's skin comes in contact with electrodes which are used to pass electrical through the user's body to measure impedance. A conductive material such as an electrode when placed next to an electrical field emitted by the touch screen sensor will interfere with the electrical field and cause the touch screen to give false readings and interfere with the user's ability to provide touch input.

Due to the technological hurdle of using BIA technology with touch screen devices, BIA capable weighing scales must employ one or more physical inputs such as buttons to modulate the functions of the scale. Displaying biometric data on an LCD screen and manipulating the data with one or more buttons can become quite laborious. For this reason, users may resort to bending over and operating the inputs with their hands. For some users, this difficulty in operating the physical inputs can lead to infrequent monitoring of their biometric data and a diminished health and body awareness. Another drawback to the inability to use BIA technology with touch screen devices is that touch screens provide a graphical interface adept at displaying graphics such as charts and graphs. Typically, in order to view detailed biometric data, the data must be transmitted to an external electrical device such as a smart phone, desktop computer, tablet computer, and the like from which to view the detailed data.

Therefore, a need exists for weighing scales that are able to provide BIA biometric data with a touch screen input. There is a further need for a weighing scale that is able to provide BIA biometric data with a touch screen input that may be operated without requiring a user to bend over to manipulate the input. There further exists a need for a device that has the capability to share fitness and other body metrics information with friends and family in order to compare how each other is performing against their fitness and health goals. Finally, there exists a need for a device that combines all the body metric data elements associated with an individual's weight and body and display all of them (graphs, charts, data analysis) on the weighing scale, rather than having a user transmit the data to an external electrical device such as a smart phone, desktop computer, tablet computer, and the like from which to view the detailed data.

BRIEF SUMMARY OF THE INVENTION

A touch input biometric apparatus for measuring and communicating biometric data of a user is provided. In preferred embodiments, the apparatus may comprise: a platform; a touch screen display integrated into the top surface of the platform and configured to receive touch input from a user; a first and a second BIA measurement zone comprising an electrically conductive material integrated into the top surface of the platform and configured to transfer an electrical current through the body of a user, said electrically conductive material electrically coupled to a BIA sensor configured to measure electrical impedance. The apparatus may calculate and display the user's estimation of percent body fat, or other biometric data on the touch screen display.

In further preferred embodiments, a touch input biometric apparatus for measuring and communicating biometric data may comprise: a platform configured to receive the weight of a user; a touch screen display integrated into the top surface of the platform and configured to receive touch input from a user; a first and a second BIA measurement zone comprising an electrically conductive material integrated into the top surface of the platform and configured to transfer an electrical current through the body of a user, said electrically conductive material electrically coupled to a BIA sensor configured to measure electrical impedance; and a weight sensor configured to measure the weight of the user on the platform. The apparatus may display the user's weight, estimation of percent body fat, or other biometric data on the touch screen display.

In further preferred embodiments, the platform comprises an electrically insulating region positioned between the electrically conductive material of the first BIA measurement zone and the electrically conductive material of the second BIA measurement zone. The electrically insulating region may extend around a distal edge of the touch screen display and may electrically insulate the touch screen display from the first BIA measurement zone and second BIA measurement zone.

In still further preferred embodiments, a system is provided for measuring, calculating, and digitally storing a user's weight and percent body fat; the system having a touch input biometric apparatus with a touch screen display, a weight sensor, a BIA sensor, onboard memory, and a processing unit wherein the processing unit is configured to: display a login request on the touch screen; receive touch screen input from a user on the touch screen; access a user's account profile in the digital memory; calculate the user's weight using the weight sensor; calculate the user's estimated percent body fat using the BIA sensor; display the user's weight and estimated percent body fat on the touch screen; and store the user's weight and estimated percent body fat in the onboard memory.

In still further embodiments, the touch input biometric apparatus of the system further comprises a radio with a transmitter configured transmit data to an electronic device wherein the data comprises the user's calculated weight and estimated percent body fat.

In still further embodiments, the processing unit of the touch input biometric apparatus of the system is further configured to retrieve data from the memory and display the data onto the touch screen wherein the data comprises historical weight measurements and percent body fat measurements of an active user logged into the apparatus.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

Definitions

Figure 1:
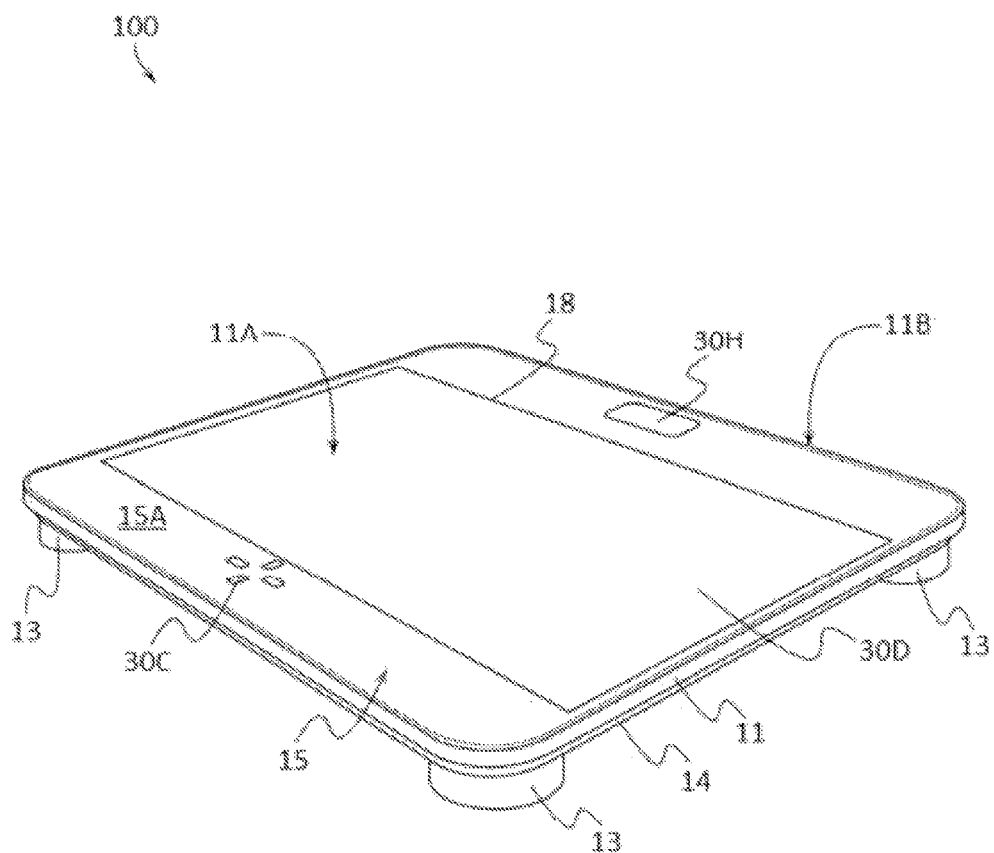
FIG. 1 depicts a perspective view of an example of a touch input biometric apparatus according to various embodiments described herein.

As used herein, the term "computer" refers to a machine, apparatus, or device that is capable of accepting and performing logic operations from software code. The term "software", "software code" or "computer software" refers to any set of instructions operable to cause a computer to perform an operation. Software code may be operated on by a "rules engine" or processor. Thus, the methods and systems of the present invention may be performed by a computer based on instructions received by computer software.

The term "electronic device" or sometimes just "device" as used herein is a type of computer generally operated by a person. Non-limiting examples of client devices include; personal computers (PCs), workstations, laptops, tablet PCs including the iPad, cell phones including iOS phones made by Apple Inc., Android OS phones, Microsoft OS phones, Blackberry phones, wearable fitness or activity trackers, or generally any electronic device capable of running computer software and displaying information to a user. Certain types of client devices which are portable and easily carried by a person from one location to another may sometimes be referred to as a "mobile device". Some non-limiting examples of mobile devices include; cell phones, smart phones, tablet computers, laptop computers, wearable computers such as watches, Google Glasses, etc. and the like.

As used herein the term "data network" or "network" shall mean an infrastructure capable of connecting two or more computers such as client devices either using wires or wirelessly allowing them to transmit and receive data. Non-limiting examples of data networks may include the internet or wireless networks or (i.e. a "wireless network") which may include wifi and cellular networks.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

New biometric recording apparatuses and methods are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

Figure 2:
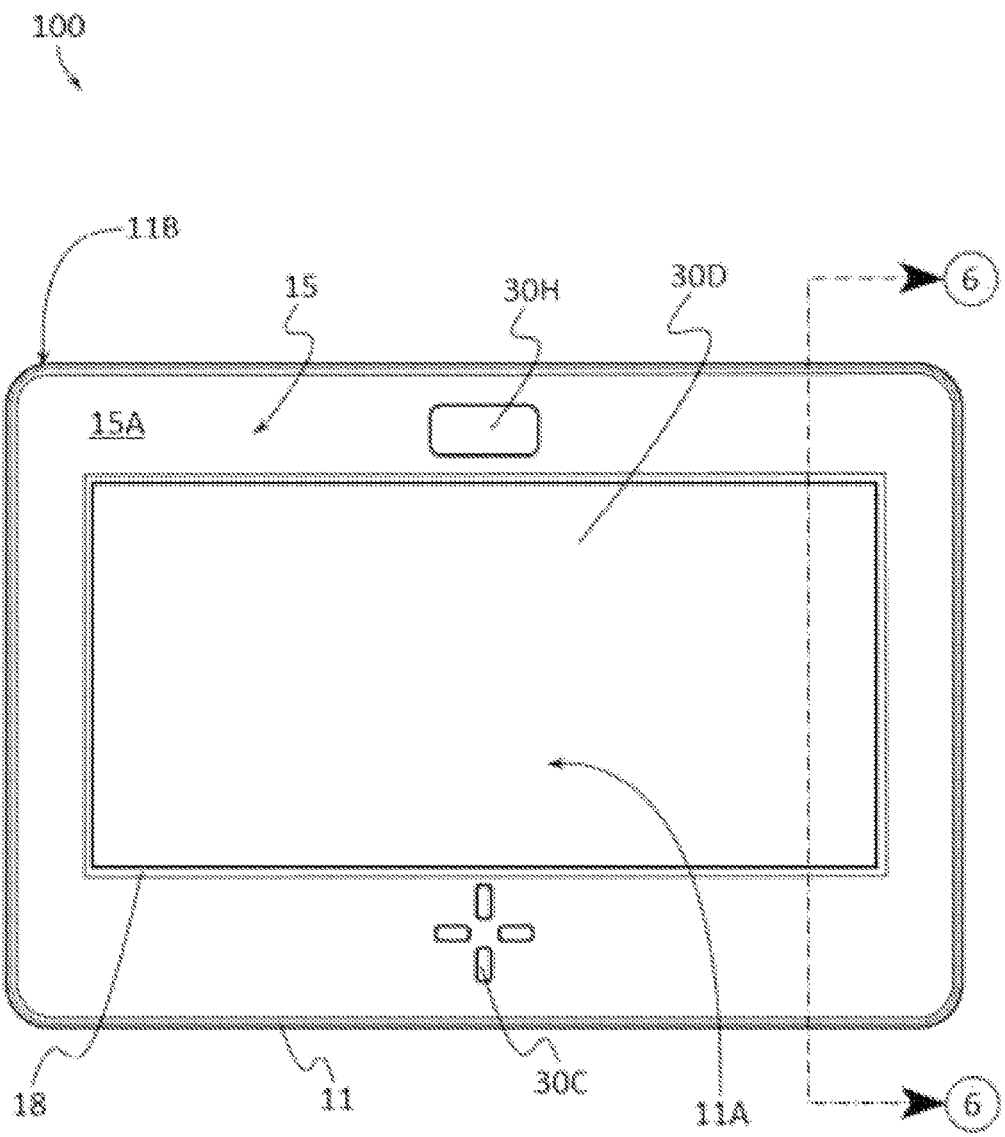
FIG. 2 illustrates a plan view of the top of an example of a touch input biometric apparatus according to various embodiments described herein.

The present invention will now be described by example and through referencing the appended figures representing preferred and alternative embodiments. FIG. 1 and FIG. 2 illustrate an example of a touch input biometric apparatus ("the apparatus") 100 according to various embodiments. As used herein the term "biometric" or "biometrics" shall generally refer to measurable physical attributes of a user, such as the user's body fat percentage or the user's weight. In this example, the apparatus 100 comprises a platform 11 configured to receive the weight of a user which may be made from glass, plastic, or other material. A touch screen display 30D may receive touch input and be integrated into the top surface 11A of the platform 11 so that a user may interact with the touch screen display by touching portions of the top surface 11A. The platform 11 may comprise a distal edge 11B that extends around the perimeter of the top surface 11A of the platform. In other embodiments, a platform 11 may be configured to comprise the touch screen display 30D of a smart phone, tablet computer, or other similar electronic device, and the platform may not be configured to support the weight of a user.

In preferred embodiments, a touch screen display 30D may comprise a resistive or capacitive touch screen which may typically comprise four layers: a top polyester coated with a transparent metallic conductive coating on the bottom; an adhesive spacer; a glass layer coated with a transparent metallic conductive coating on the top; and an adhesive layer on the backside of the glass for mounting. When a user touches the surface, the touch screen display 30D may record the change or disturbance in the electrical field that flows through the display to receive the touch input from the user. In other embodiments, the touch screen display 30D may be configured with a variety of touch screen technologies that have different methods of sensing touch such as capacitive sensing, surface capacitive touch sensing, surface acoustic wave sensing, projected capacitance sensing, mutual capacitance sensing, self-capacitance sensing, infrared grid sensing, infrared acrylic projection sensing, optical imaging, dispersive signal sensing, acoustic pulse recognition sensing, or any other suitable tactile input that may detect touch input on a display device. A touch screen display 30D may also comprise a display device such as a Liquid Crystal Display (LCD), a Cathode ray tube (CRT) display, a Field emission display (FED), a Vacuum fluorescent display (VFD), a Surface-conduction electron-emitter display (SED), a thin or thick film electro-luminescence (EL) display, an inorganic or organic light emitting diode (LED, OLED) display, a Plasma display panel (PDP), a gas discharge display (Nixie tube), or any other suitable display for outputting visual information.

The apparatus 100 may comprise one or more support legs 13 which may be coupled to the platform 11 and/or the base 14. In preferred embodiments, the apparatus 100 may comprise a base 14 configured to contain electronic elements and may be supported over a surface by four support legs 13 coupled to the base 14. The platform 11 may be supported by the base 14. The base 14 and support legs 13 may be made from plastic, metal, glass, or other suitable rigid materials and may optionally comprise flexible materials such as flexible plastics, rubber, silicone, and the like.

One or more sound devices 30H may be positioned on the apparatus 100 which may be configured to produce sounds audible to a user. In preferred embodiments, a sound device 30H may be positioned on the top surface 11A and may comprise a speaker which may be used to produce a plurality of sounds at a plurality of volume levels. In other embodiments, a sound device 30H may comprise a buzzer, a piezoelectric sound producing device, a dielectric elastomer sound producing device, a buzzer, a moving coil loudspeaker, an electrostatic loudspeaker, an isodynamic loudspeaker, a piezo-electric loudspeaker, or any other device capable of producing one or more sounds.

In further embodiments, the apparatus 100 may comprise one or more user control inputs 30C such as turnable control knobs, depressable button type switches, slide type switches, rocker type switches, or any other suitable input that may be used to modulate an electrical element or function of the apparatus 100 in addition to the input received through the touch screen display 30D.

Figure 3:
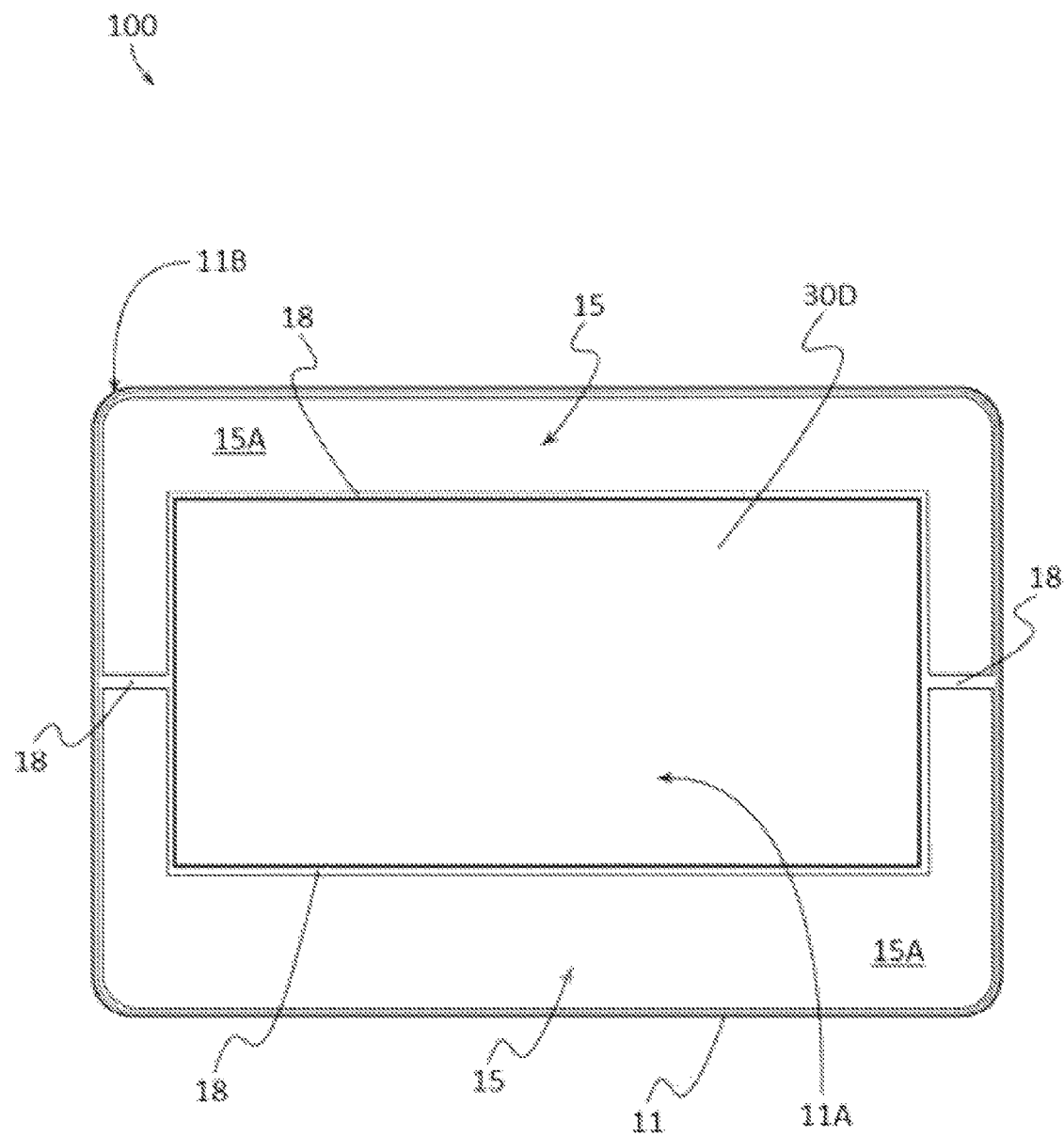
FIG. 3 shows a plan view of the top of an example of a touch input biometric apparatus according to various embodiments described herein.
Figure 4:
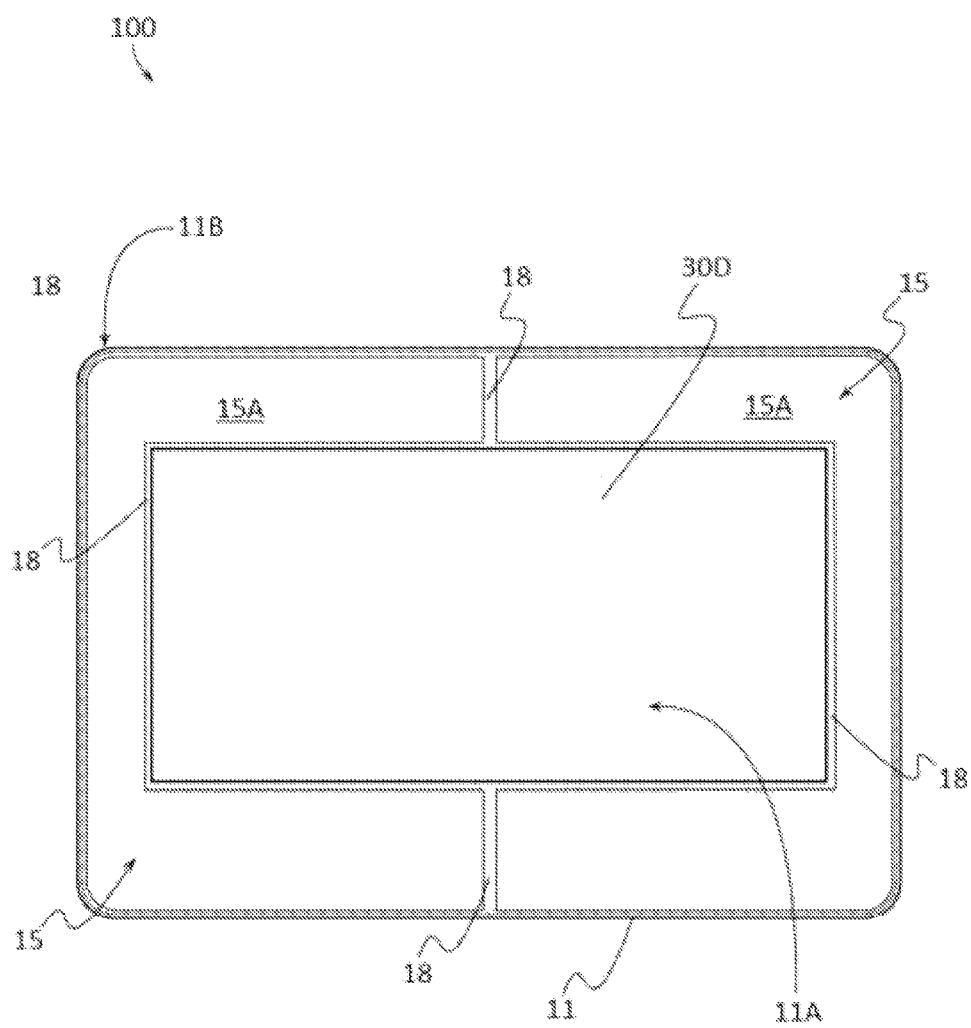
FIG. 4 a plan view of the top of an example of a touch input biometric apparatus according to various embodiments described herein.
Figure 5:
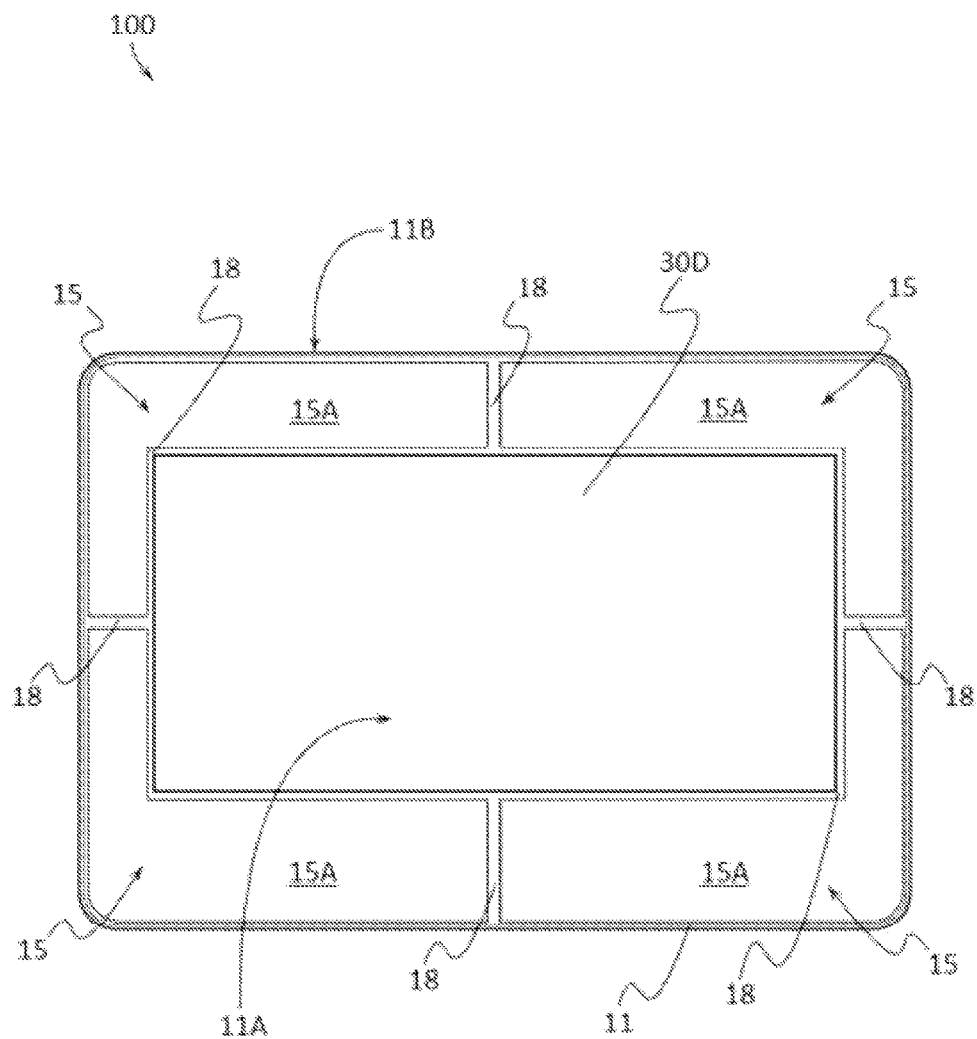
FIG. 5 illustrates a plan view of the top of an example of a touch input biometric apparatus according to various embodiments described herein.

Turning now to FIGS. 3-5, a plan view of the top of some examples of a touch input biometric apparatus 100 according to various embodiments are shown. The apparatus 100 may comprise one or more Bio-Impedance Electrical Analysis (BIA) measurement zones 15 integrated into the top surface 11A of the distal edge 11B of the platform 11. A BIA measurement zone 15 may comprise an electrically conductive material 15A such as indium tin oxide, other transparent conducting oxides, aluminum, copper, other metals or metal alloys, or any other suitable electronically conductive material. In preferred embodiments, an electronically conductive material includes one or more electrodes configured to contact portions of a user's body such as one or more hands or feet that may be in contact with a BIA measurement zone 15.

In some embodiments and as depicted in FIG. 3, the apparatus 100 may comprise two BIA measurement zones 15 on the top surface 11A and positioned along the distal edge 11B of the platform 11. The BIA measurement zones 15 may be positioned adjacent to the touch screen display 30D and on one or more sides of the touch screen display 30D. The BIA measurement zones 15 may be laterally separated from each other by an electrically insulating region 18 which may also extend around the top surface 11A comprising the integrated touch screen display 30D, thereby electrically insulating the two BIA measurement zones 15 from each other and from the touch screen display 30D. In preferred embodiments, the platform 11 may be made from electrically insulating glass or plastic and the BIA measurement zones 15 may comprise an electrically conductive material such as indium tin oxide so that the electrically insulating region 18 may be formed by the regions of the platform 11 that do not comprise an electrically conductive material 15A. In other embodiments, an electrically insulating region 18 may be made from plastic, rubber, resins, or any other suitable material may act as an electrical insulator or that has a low electrical conductivity value.

In preferred embodiments, the electrically insulating region 18 may extend around the distal edge 11B of the touch screen display 30D and electrically insulate the touch screen display 30D from a first BIA measurement zone 15 and a second BIA measurement zone 15. In further preferred embodiments, an electrically insulating region 18 may separate a BIA measurement zone 15 from a second BIA measurement zone 15 by a distance of two to five millimeters. In other embodiments, an electrically insulating region 18 may separate a BIA measurement zone 15 from a second BIA measurement zone 15 by a distance of 0.1 to fifty millimeters. In further preferred embodiments, an electrically insulating region 18 may separate a BIA measurement zone 15 from the top surface 11A comprising the integrated touch screen display 30D by a distance of two to five millimeters. In other embodiments, an electrically insulating region 18 may have a width defined by the distance separating a BIA measurement zone 15 from the top surface 11A comprising the integrated touch screen display 30D, or the distance between a first and second BIA measurement zone 15. In some embodiments, the width of the electrically insulation region 18 or the distance between a BIA measurement zone 15 and touch screen display 30D may be 0.1 to one hundred millimeters, or 0.1 to 50 millimeters, or 0.1 to 10 millimeters, or other suitable widths or distances capable of electrically insulating the touch screen display 30D from a BIA measurement zone 15.

In alternative embodiments and as illustrated in FIG. 4, the apparatus 100 may comprise two BIA measurement zones 15 on the top surface 11A of the distal edge 11B of the platform 11. The BIA measurement zones 15 may be longitudinally separated from each other by an electrically insulating region 18 which may also extend around the top surface 11A comprising the integrated touch screen display 30D, thereby electrically insulating the two BIA measurement zones 15 from each other and from the adjacent touch screen display 30D.

In further embodiments and as shown in FIG. 5, the apparatus 100 may comprise four BIA measurement zones 15 on the top surface 11A positioned along the distal edge 11B of the platform 11. The BIA measurement zones 15 may be longitudinally and laterally separated from each other by an electrically insulating region 18 which may also extend around the top surface 11A comprising the integrated touch screen display 30D, thereby electrically insulating the two BIA measurement zones 15 from each other and from the touch screen display 30D.

In still further embodiments, one or more BIA measurement zones 15 may be placed in any other orientation around and adjacent to a touch screen display 30D on a top surface 11A along the distal edge 11B of the platform 11. For example, one or more BIA measurement zones 15 may be placed adjacent to the touch screen display 30D on a single side of the touch screen display 30D. In another example, one or more BIA measurement zones 15 may be placed adjacent to the touch screen display 30D on opposite sides of the touch screen display 30D.

Figure 6:
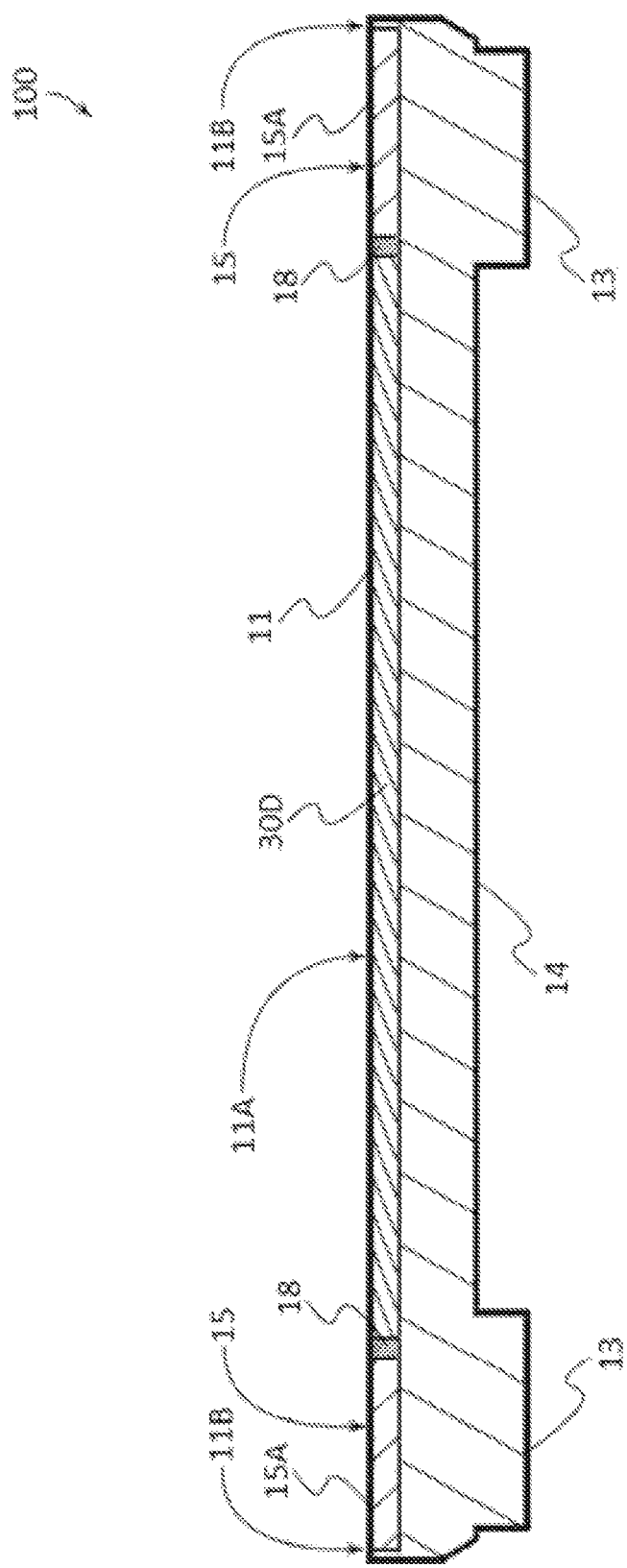
FIG. 6 shows a sectional, through line 6-6 shown in FIG. 2, elevation view of an example of a touch input biometric apparatus according to various embodiments described herein.

FIG. 6 shows a sectional, through line 6-6 shown in FIG. 2, elevation view of an example of a touch input biometric apparatus 100 according to various embodiments described herein. In this embodiment, the electrically conductive material 15A of the Bio-Impedance Electrical Analysis (BIA) measurement zones 15, the electrically insulating region 18, and the touch screen display 30D are coupled to the base 14 to provide a generally planar top surface 11A. In other embodiments, the electrically conductive material 15A of the Bio-Impedance Electrical Analysis (BIA) measurement zones 15 may be coupled to the top surface 11A while leaving an electrically insulating region 18 to separate the Bio-Impedance Electrical Analysis (BIA) measurement zones 15 from the top surface 11A that is integrated with the touch screen 30D.

As perhaps best shown in FIG. 6, the touch screen display 30D may be integrated into the platform 11 so that when a user touches portions of the top surface 11A over the touch screen display 30D, the touch input may be received by the touch screen display 30D. Other elements of the apparatus 100 such as the electrically conductive material 15A of BIA measurement zones 15 and the electrically insulating regions 18 may be integrated into the platform 11 so that they are coplanar with the top surface 11A, thereby forming a generally planar surface for the user to touch or stand on.

Figure 7:
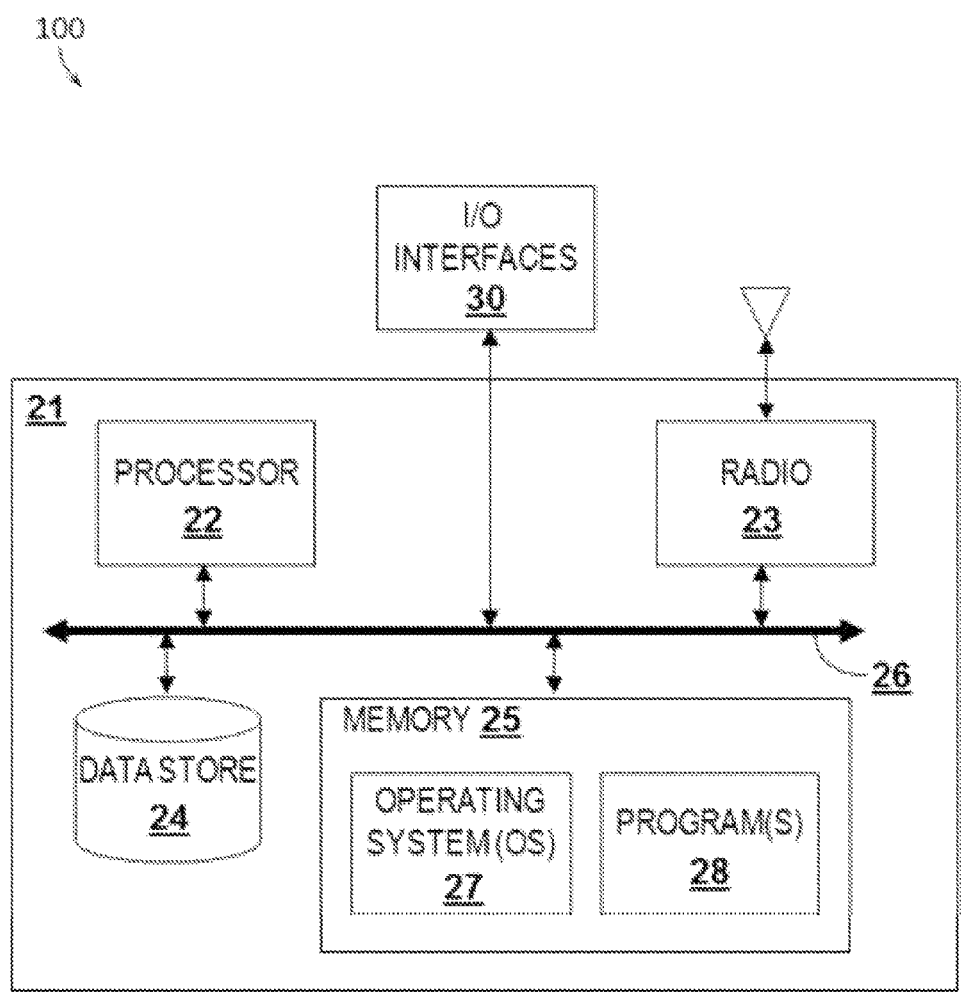
FIG. 7 depicts a block diagram showing an example of some of the electronic elements a touch input biometric apparatus may comprise according to various embodiments described herein.

FIG. 7 depicts a block diagram showing an example of some of the electronic elements a touch input biometric apparatus 100 may comprise according to various embodiments described herein. In some embodiments and in the present example, the apparatus 100 can be a digital device that, in terms of hardware architecture, comprises a processing unit 21 which generally includes a processor 22, input/output (I/O) interfaces 30, an optional radio 23, a data store 24, and memory 25. It should be appreciated by those of ordinary skill in the art that FIG. 7 depicts the apparatus 100 in an oversimplified manner, and a practical embodiment may include additional components or elements and suitably configured processing logic to support known or conventional operating features that are not described in detail herein. The components and electrical elements (22, 30, 23, 24, and 25) are communicatively coupled via a local interface 26. The local interface 26 can be, for example but not limited to, one or more buses or other wired or wireless connections configured to provide electrical communication, as is known in the art. The local interface 26 can have additional elements, which are omitted for simplicity, such as controllers, buffers (caches), drivers, repeaters, and receivers, among many others, to enable communications. Further, the local interface 26 may include address, control, and/or data connections to enable appropriate communications among the aforementioned components.

The processor 22 is a hardware device for executing software instructions. The processor 22 can be any custom made or commercially available processor, a central processing unit (CPU), an auxiliary processor among several processors associated with the processing unit 21, a semiconductor-based microprocessor (in the form of a microchip or chip set), or generally any device for executing software instructions. When the processing unit 21 is in operation, the processor 22 is configured to execute software stored within the memory 25, to communicate data to and from the memory 25, and to generally control operations of the apparatus 100 pursuant to the software instructions. In an exemplary embodiment, the processor 22 may include a mobile optimized processor such as optimized for power consumption and mobile applications. The I/O interfaces 30 can be used to record biometric data and to receive user input from a control input 30C or a touch screen display 30D and/or for providing system output through the display screen 12. The I/O interfaces 30 can also include, for example, a serial port, a parallel port, a small computer system interface (SCSI), an infrared (IR) interface, a radio frequency (RF) interface, a universal serial bus (USB) interface, and the like.

An optional radio 23 enables wireless communication to an external access electronic device or network. In some embodiments, a radio may operate on a cellular band and may communicate with or receive a Subscriber Identity Module (SIM) card or other wireless network identifier. Any number of suitable wireless data communication protocols, techniques, or methodologies can be supported by the radio 23, including, without limitation: RF; IrDA (infrared); Bluetooth; WiFi; ZigBee (and other variants of the IEEE 802.15 protocol); IEEE 802.11 (any variation); IEEE 802.16 (WiMAX or any other variation); Direct Sequence Spread Spectrum; Near-Field Communication (NFC); Frequency Hopping Spread Spectrum; Long Term Evolution (LTE); cellular/wireless/cordless telecommunication protocols (e.g. 3G/4G, etc.); wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; and any other protocols for wireless communication. The data store 24 may be used to store data. The data store 24 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 24 may incorporate electronic, magnetic, optical, and/or other types of storage media. In preferred embodiments, the radio 23 may comprise a Bluetooth receiver and a Bluetooth transmitter allowing the radio to send and receive data through Bluetooth data communication protocols. In further preferred embodiments, the radio 23 may comprise a WiFi receiver and a WiFi transmitter allowing the radio to send and receive data through WiFi data communication protocols.

The memory 25 may include any of volatile memory elements (e.g., random access memory (RAM, such as DRAM, SRAM, SDRAM, etc.)), nonvolatile memory elements (e.g., ROM, hard drive, etc.), and combinations thereof. Moreover, the memory 25 may incorporate electronic, magnetic, optical, and/or other types of storage media. Note that the memory 25 may have a distributed architecture, where various components are situated remotely from one another, but can be accessed by the processor 22. The software in memory 25 can include one or more software programs, each of which includes an ordered listing of executable instructions for implementing logical functions. In the example of FIG. 7, the software in the memory 25 includes a suitable operating system (O/S) 27 and programs 28. The operating system 27 essentially controls the execution of input/output interface 30 functions, and provides scheduling, input-output control, file and data management, memory management, and communication control and related services. The operating system 27 may be, for example, LINUX (or another UNIX variant), Android (available from Google), Symbian OS, Microsoft Windows CE, Microsoft Windows 7 Mobile, iOS (available from Apple, Inc.), webOS (available from Hewlett Packard), Blackberry OS (Available from Research in Motion), and the like. The programs 28 may include various applications, add-ons, etc. configured to provide end user functionality with the apparatus 100. For example, exemplary programs 28 may include, but not limited to, environmental variable analytics and modulation of input/output interface 30 functions. In a typical example, the end user typically uses one or more of the programs 28 to record biometric data such as body weight and percent body fat, to manipulate the data for display on a touch screen display 30D, and to import and export the data from the apparatus 100.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer readable storage medium having stored therein a corresponding set of computer instructions that upon execution would cause an associated processor to perform the functionality described herein. Thus, the various aspects of the invention may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

The processing unit 21 may also include a main memory, such as a random access memory (RAM) or other dynamic storage device (e.g., dynamic RAM (DRAM), static RAM (SRAM), and synchronous DRAM (SDRAM)), coupled to the bus for storing information and instructions to be executed by the processor 22. In addition, the main memory may be used for storing temporary variables or other intermediate information during the execution of instructions by the processor 22. The processing unit 21 may further include a read only memory (ROM) or other static storage device (e.g., programmable ROM (PROM), erasable PROM (EPROM), and electrically erasable PROM (EEPROM)) coupled to the bus for storing static information and instructions for the processor 22.

Figure 8:
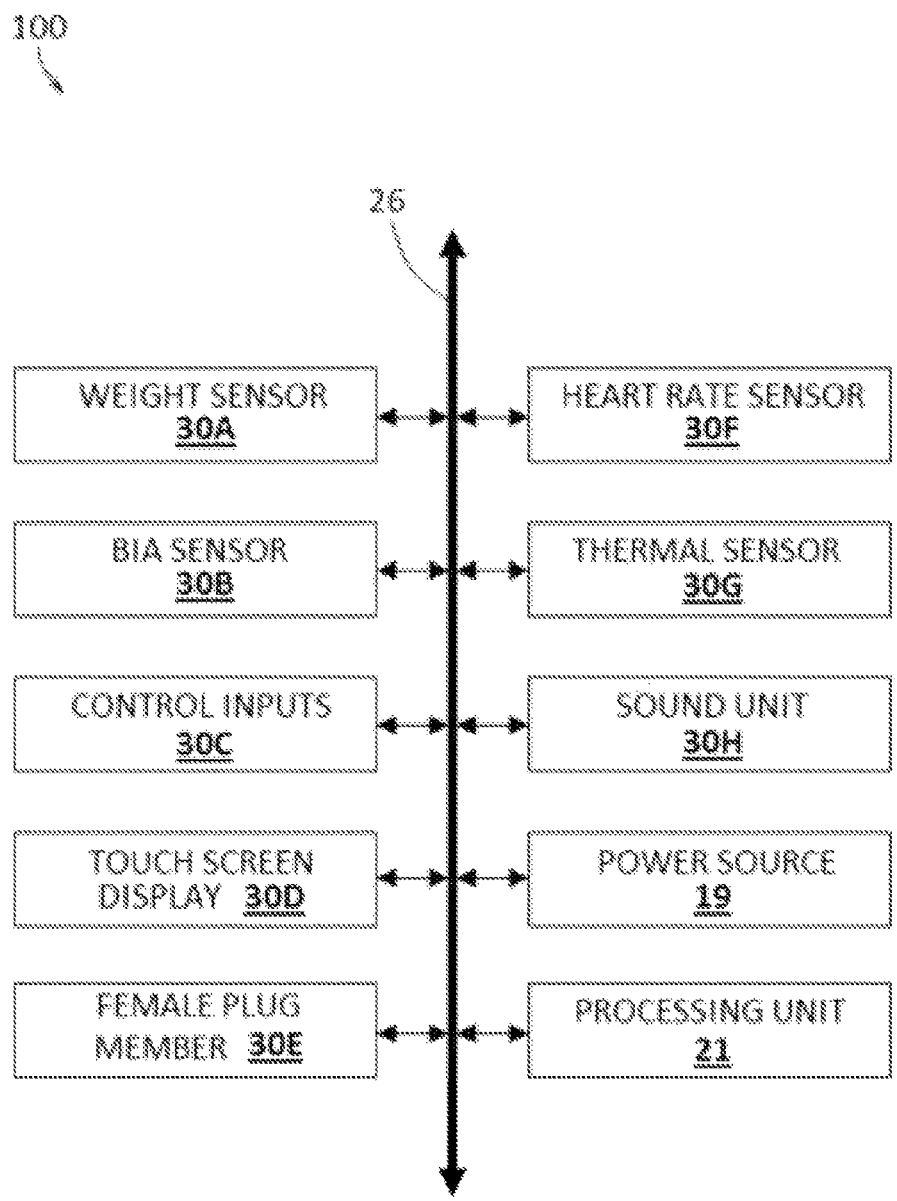
FIG. 8 illustrates a block diagram showing an example of some of the input/output interfaces that may be in electrical communication with a processing unit of a touch input biometric apparatus according to various embodiments described herein.

FIG. 8 illustrates a block diagram showing an example of some of the input/output interfaces 30 that may be in electrical communication with a processing unit 21 of a touch input biometric apparatus according to various embodiments described herein. In preferred embodiments, an apparatus 100 may comprise one or more input/output interfaces such as a weight sensor 30A, BIA sensor 30B, control input 30C, touch screen display 30D, female plug member 30E, heart rate sensor 30F, thermal sensor 30G, and/or sound device 30H. The input/output interfaces may be communicatively coupled to a processing unit 21 via a local interface 26. Additionally, one or more power sources 19 may also be coupled to a processing unit 21 and the input/output interfaces via a local interface 26.

The weight sensor 30A or load cell can be a number of different devices for converting a pressure or a force into an electrical signal as known in the art. As such, the weight sensor 30A may compromise a Wheatstone bridge configuration employing piezoresistive elements or other pressure converting devices to provide a varying electrical signal indicative of the weight of a user on the platform 11. In some embodiments, the weight sensor 30A may supply an analog signal in terms of a voltage or a current having a magnitude which varies according to the weight of the of a user on the platform 11. This analog signal cannot be easily converted for digital display purposes without the use of an analog to digital converter (A/D converter). Essentially, the prior art shows many techniques for performing analog to digital conversion, any of which may be used herein. Such devices respond to an analog signal to provide a digital code or a digital signal, which can be processed by the processing unit 21 to eventually activate touch screen display 30A preferably allowing the weight of the user to be displayed on the touch screen display 30A.

A Bio-Impedance Electrical Analysis (BIA) sensor 30B may preferably comprise a volt meter in electrical communication with two or more electrodes which may be provided by the electrically conductive material 15A of two or more Bio-Impedance Electrical Analysis (BIA) measurement zones 15 (FIGS. 3-6). In further embodiments, the electrically conductive material 15A of a first BIA measurement zone 15 may be electrically coupled to a first electrode and the electrically conductive material 15A of the second BIA measurement zone 15 may be electrically coupled to a second electrode. The impedance of cellular tissue can be modeled as a resistor (representing the extracellular path) in parallel with a resistor and capacitor in series (representing the intracellular path). This results in a change in impedance versus the frequency used in the measurement. The impedance measurement is generally measured from the one area of the body to another area such as one foot to another foot and preferably uses either two or four electrodes. A small current on the order of 1-10 μA may be passed between two electrodes, and the voltage may be measured between the same (for a two electrode configuration) or between the other two electrodes to determine the electrical impedance between the electrodes. The electrical impedance, or opposition to the flow of an electric current through body tissues can then be used to calculate an estimate of total body water (TBW) and the percent body fat of the user according to algorithms common in the art. In preferred embodiments, one or more BIA measurement zones 15 may be configured to send or receive an electric current allowing a BIA measurement zone 15 to function as a reversible polarity electrode.

In some embodiments, the apparatus may comprise a female plug member 30E which may be configured to receive and electrically communicate with a male plug member. The female plug member 30E may allow data such as biometric data to be wiredly imported and exported from the data store 24 (FIG. 7) of the apparatus 100. In preferred embodiments, a female plug member 30E may comprise a USB such as a female micro-USB connector or female mini-USB connector. In other embodiments, an electronic device power supply 14 may comprise a female Type A USB connector, a female Type B USB connector, a female Mini-A USB connector, a female Mini-B USB connector, a female Micro-A USB connector, a female Micro-B USB connector, a female Micro-B USB 3.0 connector, a female ExtMicro USB connector, a female Lightning connector, a female 30-pin dock connector, a female Pop-Port connector, a female Thunderbolt connector, a female Firewire connector, a female Portable Digital Media Interface (PDMI) connector, a female coaxial power connector, a female barrel connector, a female concentric barrel connector, a female tip connector, or any other plug, connector, or receptacle capable of electrical communication with an electronic device.

The apparatus 100 may comprise a heart rate sensor 30F. In preferred embodiments, a heart rate sensor 30F may comprise a probe which may be integrated into the top surface 11A and configured to contact portions of a user in contact with the platform 11. The probe may be configured to emit light at two wavelengths (650 nm and 805 nm). The light may be partly absorbed by haemoglobin, by amounts which differ depending on whether it is saturated or desaturated with oxygen. By calculating the absorption at the two wavelengths the heart rate sensor 30F and/or the processing unit 21 may compute the proportion of haemoglobin which is oxygenated. The heart rate sensor 30F and/or the processing unit 21 may be configured to distinguishing pulsatile flow from other more static signals (such as tissue or venous signals) to determine the heart rate of the user. In other embodiments, a heart rate sensor 30F may comprise any other type of sensor capable of detecting the pulse or heart rate of a user in contact with the platform 11.

The apparatus 100 may also comprise a thermal sensor 30G. In some embodiments, a thermal sensor 30G may be configured to provide the ambient temperature of the environment that the apparatus is in. In further embodiments, a thermal sensor 30G may be configured to determine the temperature of the area of the user that is contacting a portion of the top surface 11A of the platform 11. The temperature of the area of the user can then be used to calculate an estimate of the body temperature of the user according to algorithms common in the art. In preferred embodiments, a thermal sensor 30G may comprise a thermocouple, a resistive temperature device (RTDs, thermistors), an infrared temperature sensor, a bimetallic device, a liquid expansion device, a molecular change-of-state device, a silicon diode, or any other type of temperature sensor configured to electrically communicate temperature information.

The electronic elements of the apparatus 100 may be supplied electrical power by one or more power sources 19. A power source 19 may comprise a battery or external power supply capable of supplying AC or DC electric current. In other embodiments, a power supply 19 may comprise an inductive charging or wireless power supply to transfer electrical power to the electrical elements using an electromagnetic field. A wireless charging receiver power source 19 may be configured to receive energy through an inductive coupling and to communicate the energy to the local interface 26. In other embodiments, a wireless charging power source 19 may be configured to receive energy through an inductive coupling and to communicate the energy to the local interface 26.

Figure 9:
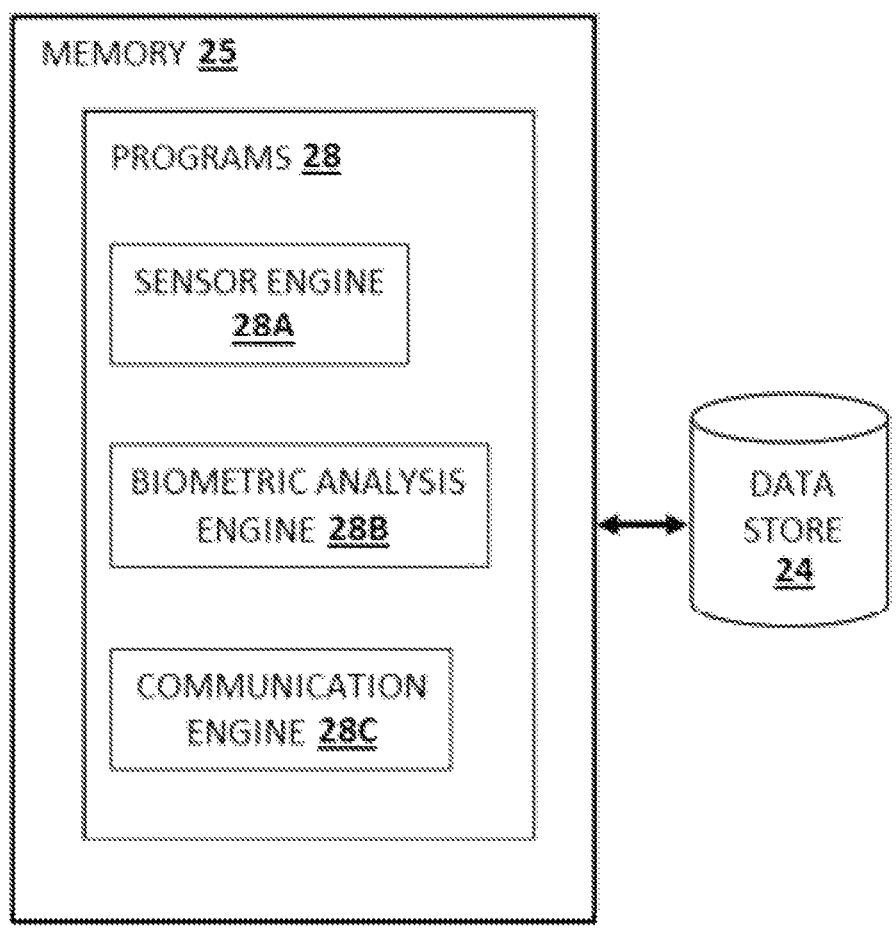
FIG. 9 shows a block diagram showing an example of some of the programs that may be performed in the memory of a processing unit according to various embodiments described herein.

FIG. 9 shows a block diagram showing an example of some of the programs 28 that may be performed in the memory 25 of a processing unit 21 according to various embodiments described herein. In preferred embodiments, the programs 28 may comprise a sensor engine 28A which may be configured to receive data from a weight sensor 30A (FIG. 8), a BIA sensor 30B (FIG. 8), a heart rate sensor 30F (FIG. 8), and/or a thermal sensor 30G (FIG. 8). In some embodiments, the sensor engine 28A may receive digital or analog data from one or more sensors and convert the digital or analog data into biometric data. In other embodiments, the sensor engine 28A may receive digital or analog biometric data from one or more sensors or from the data store 24. The sensor engine 28A may then associate the data with a particular user and store the data in the data store 24.

In further preferred embodiments, the programs 28 may comprise a biometric analysis engine 28B which may be configured to send and retrieve data from the data store 24 for a particular user that matches the user login information which may also be stored in the data store 24. In some embodiments, the biometric analysis engine 28B may be configured to receive data directly from one or more sensors and associate the data with the particular user. In other embodiments, the biometric analysis engine 28B may be configured to receive data directly from the sensor engine 28A. The biometric analysis engine 28B may then display the data for a particular user on the touch screen display 30D or otherwise manipulate the data according to input received by the user through the touch screen display 30D.

In further preferred embodiments, the programs 28 may comprise a communication engine 28C which may be configured to communicate data with the sensor engine 28A, biometric analysis engine 28B, touch screen display 30D, and/or the data store 24 to another electronic device such as a smart phone, printer, tablet computer, laptop computer, desktop computer, wearable fitness device such as a Fitbit®, Vivofit®, iFit Active®, or any other similar electronic device. In some embodiments, the communication engine 28C may be configured to send or export and receive or import data with a wireless internet data connection through the radio 23 (FIG. 7). In other embodiments, the communication engine 28C may be configured to send or export and receive or import data with a wired internet data connection through a female plug member 30E (FIG. 8). In further embodiments, the communication engine 28C may be configured to send user biometric data or touch input through a wired or wireless data internet connection to a third party such as a website, service provider, social network, commercial entity, or other digital content provider. The third party, in response to the received data, may then send advertisements, offers, or other digital content to the apparatus 100 which may be received through the wired or wireless data internet connection and displayed on the touch screen display 30D.

Figure 10:
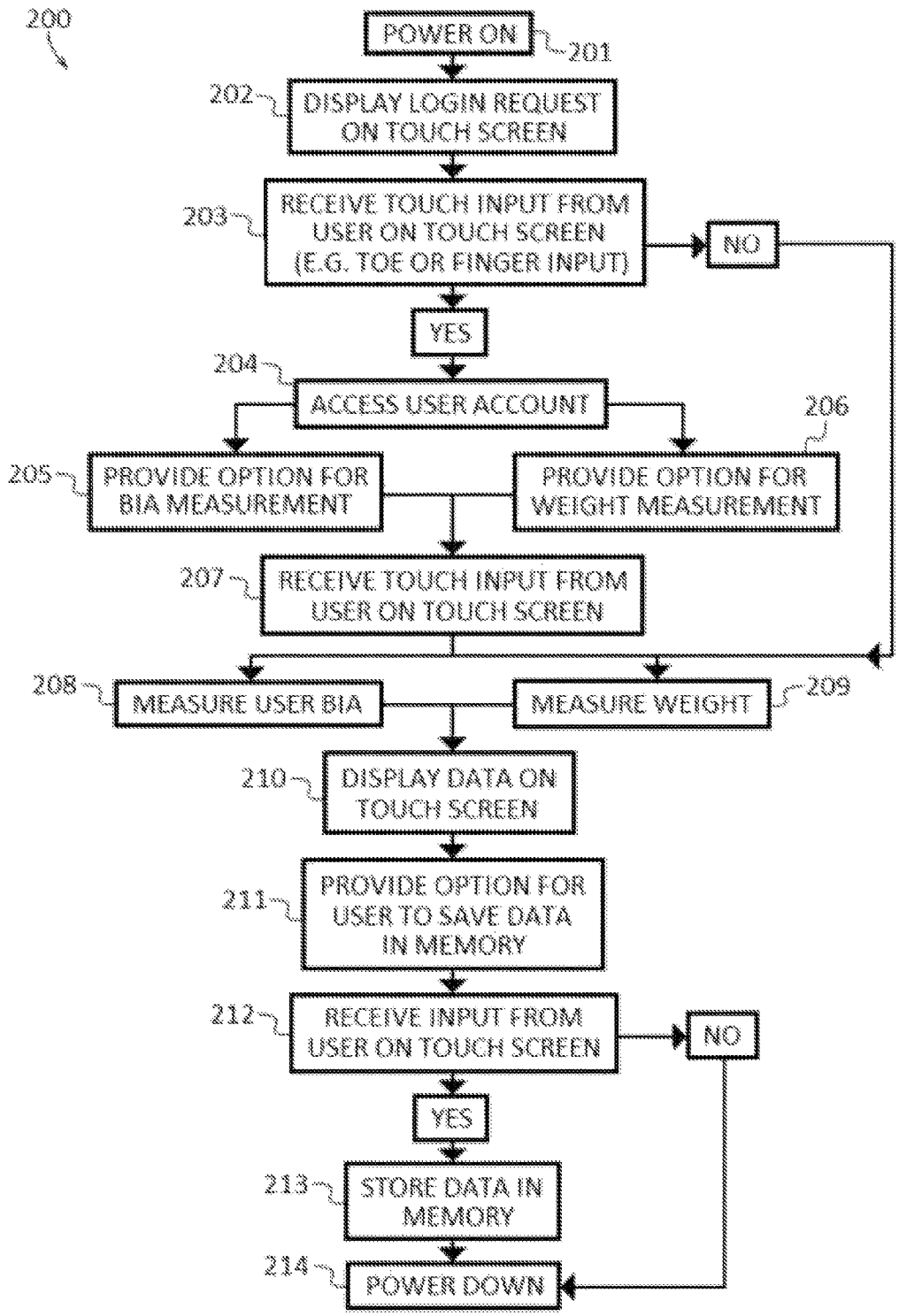
FIG. 10 depicts a flow chart of an example method for using touch input to interact with a touch input biometric apparatus according to various embodiments described herein.

Referring now to FIG. 10, a flow chart of an example method for using touch input to interact with a touch input biometric apparatus 200 according to various embodiments described herein is shown. In this embodiment, the method may begin by powering on 201 the apparatus 100 (FIGS. 1-8). The apparatus 100 may then display a login request 202 on the touch screen display 30D (FIGS. 1-6, and 8). The user may touch the touch screen display 30D to input login information for example from the touch of a toe or finger 203. The touch screen display 30D may receive the touch input which may be electrically communicated to the biometric analysis engine 28B. If the user does not provide touch input, the sensor engine 28A may measure the BIA of the user 208 and/or measure the weight 209 of the user.

If the user does provide login input through the touch screen display 203, the biometric analysis engine 28B may access the user account 204 and store and retrieve biometric data for that user in the memory 25 (FIG. 7). The option for BIA measurement 205 and/or the option from weight measurement 206 may then be provided on the touch screen display 30D (FIGS. 1-6, and 8). The user may touch the touch screen display 30D to input login information and the biometric analysis engine 28B may receive the touch input 207 and the sensor engine 28A may measure the BIA of the user 208 and/or measure the weight 209 of the user. The biometric analysis engine 28B may receive BIA data such as percent body fat of the user and/or the weight data of the user and may then display the data on the touch screen display 30D. The option to save the user data in the memory 211 may then be provided on the touch screen display 30D. The user may touch the touch screen display 30D and biometric analysis engine 28B and/or the sensor engine 28A may receive the touch input 212. If the user touches the touch screen display 30D to select to save the user data, the biometric analysis engine 28B and/or the sensor engine 28A may store the data in the memory 213 and the device may then power down 214. If the user does not touch the touch screen display 30D to select to save the user data, the data may not be stored in the memory and the device may then power down 214.

Figure 11:
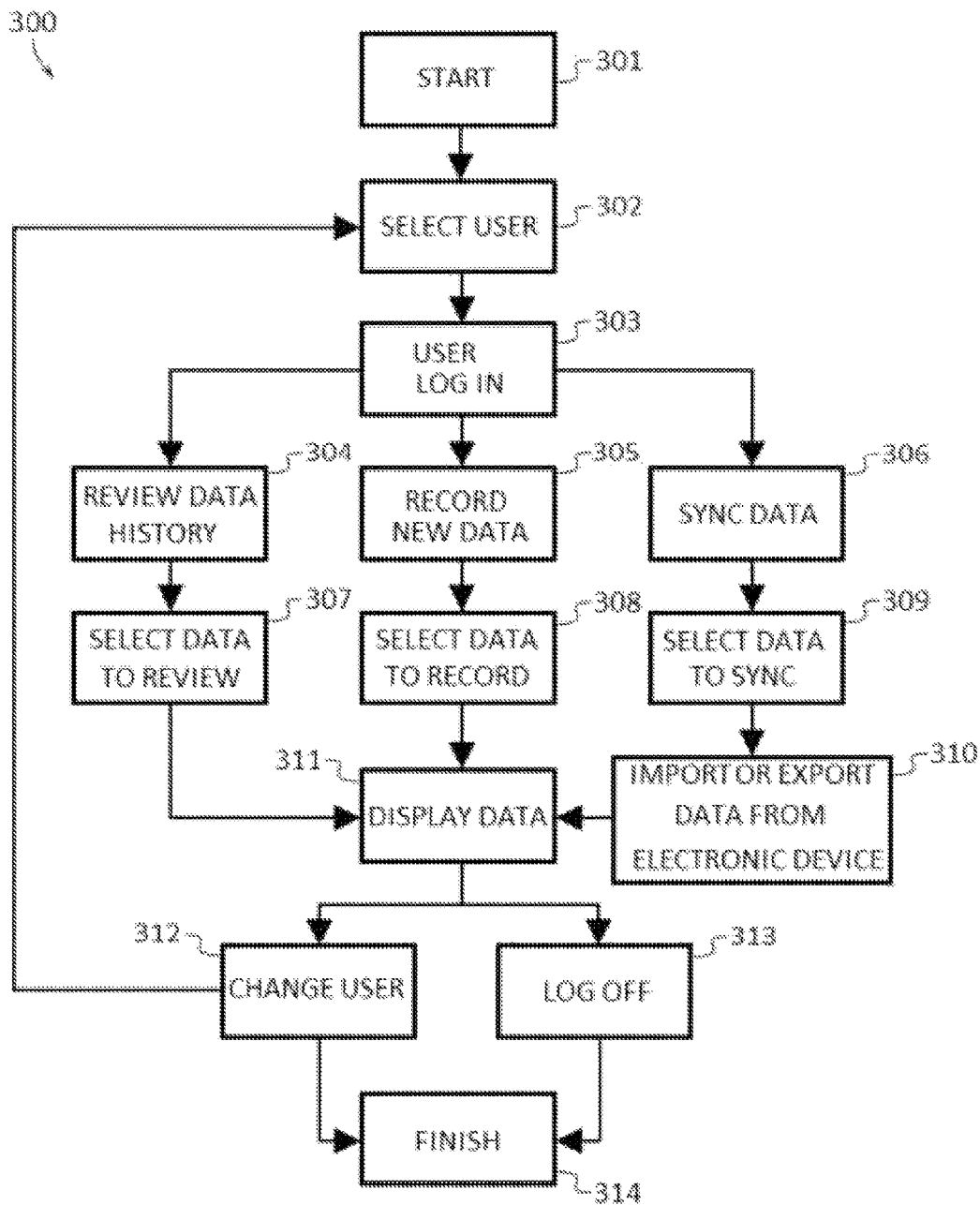
FIG. 11 illustrates a flow chart of an example method for using a touch input biometric apparatus according to various embodiments described herein.

FIG. 11 depicts a flow chart of an example method for using a touch input biometric apparatus 300 according to various embodiments described herein. In this embodiment, the method may start 301 once the user touches the platform 11 and/or the touch screen display 30D (FIGS. 1-6, and 8). The user may then be presented with the option to select a user account by the biometric analysis engine 28B on the touch screen display 30D. The user may select a user or user account 302 and optionally enter user login data by touching the touch screen display 30D and the biometric analysis engine 28B may log in the user 303 and optionally present the user with user data associated with the user account or profile that may be retrieved from the digital memory 25. The biometric analysis engine 28B may then present the user with the option to review data history 304, record new data 305, and/or sync data 306 on the touch screen display 30D. If the user uses touch input to select review data history 304, the user may further select data to review 307, the biometric analysis engine 28B may retrieve the requested data such as biometric data including historical weight measurements and percent body fat measurements of the user from the data store 24 to be displayed on the touch screen display 30D and the data may be displayed 311 on the touch screen display 30D by the biometric analysis engine 28B. If the user uses touch input to select record new data 305, the sensor engine may record new biometric data from one or more sensors according the data the user selects to record 308 and the data may be displayed 311 on the touch screen display 30D by the biometric analysis engine 28B. If the user selects to sync data 306, the user may select the data to sync 309 and optionally which electronic device with which to sync the data. The communication engine 28C may then wirelessly or wiredly import or export data such as biometric data including user weight data and percent body fat data from the electronic device to the data store 24 or biometric analysis engine 28B and the data may be displayed 311 on the touch screen display 30D by the biometric analysis engine 28B. The user may then use touch input to select to log off 313 or to change the user 312 and the process may finish 314. Optionally, the user may use touch input to select to change the user account or profile 312 and the process may continue to allow a user to be selected in step 302.

Figure 12:
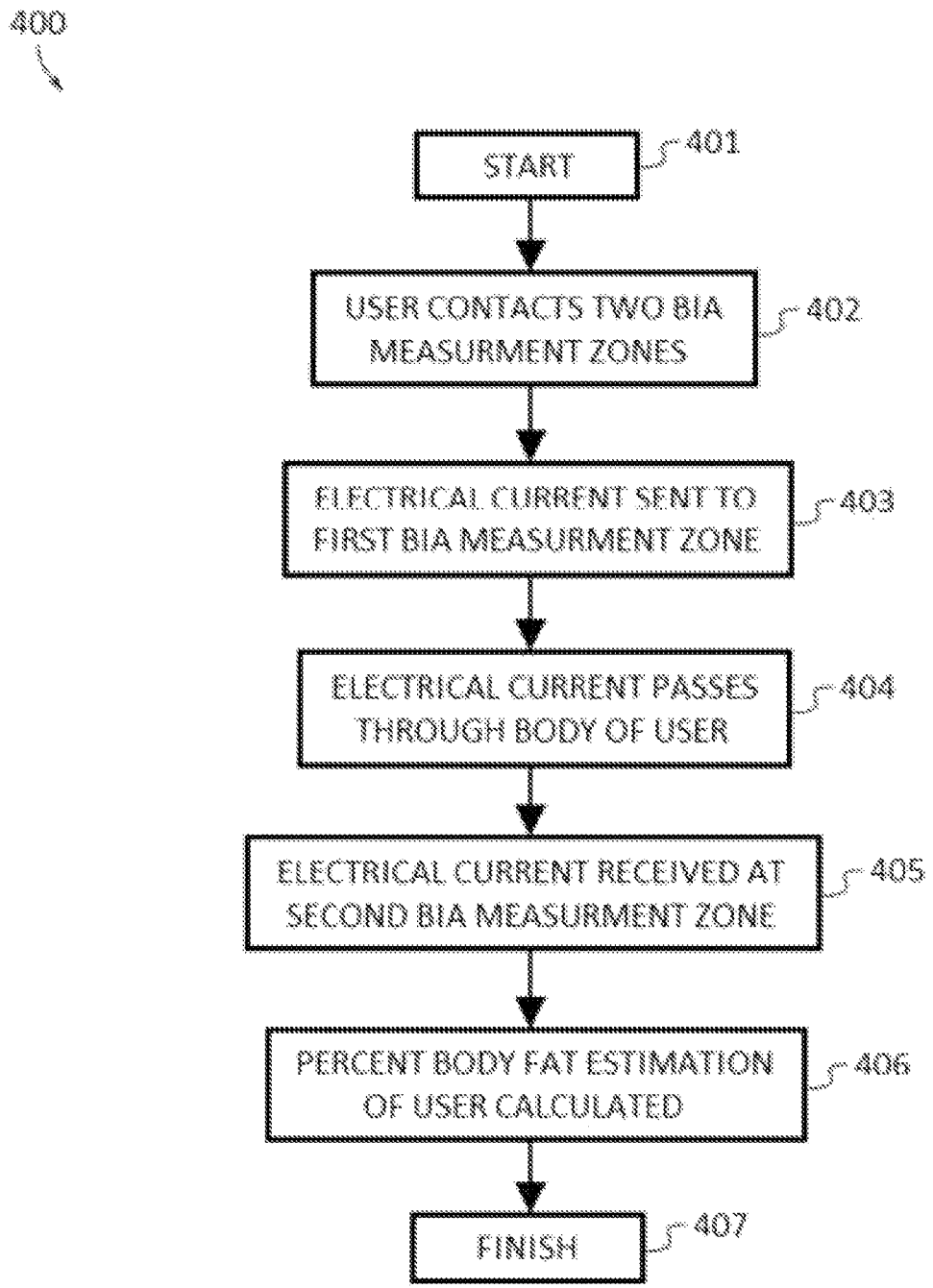
FIG. 12 shows a flow chart of an example method for obtaining an estimation of the percent body fat of a user according to various embodiments described herein.

FIG. 12 depicts a flow chart of an example method for obtaining an estimation of the percent body fat of a user 400 according to various embodiments described herein. In this embodiment, the method may start 401 when the touch screen display 30D receives touch input from a user. By way of non-limiting example, the skin of the user may physically contact two BIA measurement zones 402. The sensor engine 28A may then direct the BIA sensor 30A to send electrical current to the electrically conductive material 15A or electrode of the first BIA measurement zone 403. The electrical current may then pass from the first BIA measurement zone 403, through the body of the user 404 (e.g. through their feet or portions of their feet or optionally through hands or portions of their hands), to be received by the electrically conductive material 15A or electrode of the second BIA measurement zone 405. A voltmeter in the BIA sensor 30A may determine the electrical impedance of the user's body and the data may optionally store the data in memory 25. In some embodiments, the sensor engine 28A may receive the impedance or resistance data from the BIA sensor 30A or the memory 25 to calculate the estimate of the percent body fat of the user 406. In other embodiments, the biometric analysis engine 28B may receive the impedance or resistance data from the sensor engine 28A or the memory 25 to calculate the estimate of the percent body fat of the user 406. The estimation of the percent body fat of a user may be performed using a Bio-Impedance Electrical Analysis (BIA) equation common in the art such, for example, as Free Fat Mass=−4.104+(0.518×height(2)/resistance)+(0.231× weight)+(0.130×reactance)+(4.229×sex: men=1, women=0) where resistance or impedance is measured by the BIA sensor or any other suitable equation. The percent body fat biometric data of the user may then be stored in memory 25, displayed on the touch screen display 30D, or communicated to another electric device and the process may finish 407.

Figure 13:
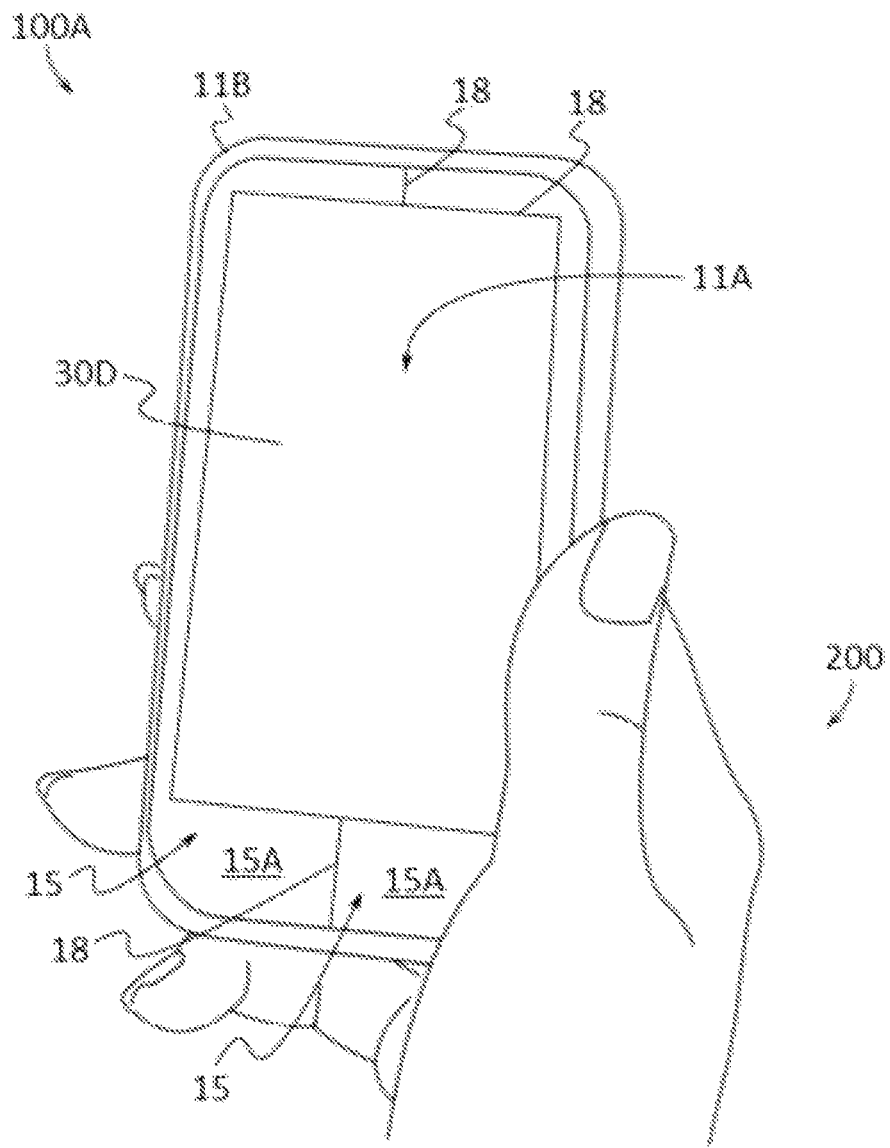
FIG. 13 depicts a perspective view of an example of a touch input biometric apparatus according to various embodiments described herein.

FIG. 13 depicts a perspective view of an example of a touch input biometric apparatus 100A that is being held by a user 200 according to various embodiments described herein. In this example, the apparatus 100A may comprise a smart phone, tablet computer, or other similar electronic device including a mobile device configured to be contacted by one or more hands of a user 200. A touch screen display 30D may receive touch input and be integrated into the top surface 11A of the apparatus 100A so that a user may interact with the touch screen display by touching portions of the top surface 11A. The apparatus 100A may comprise a distal edge 11B that extends around the perimeter of the top surface 11A of the platform.

The apparatus 100A may comprise two or more BIA measurement zones 15 on the top surface 11A and positioned along the distal edge 11B of the platform 11. The BIA measurement zones 15 may be positioned adjacent to the touch screen display 30D and on one or more sides of the touch screen display 30D. The BIA measurement zones 15 may be laterally separated from each other by an electrically insulating region 18 which may also extend around the top surface 11A comprising the integrated touch screen display 30D, thereby electrically insulating the two BIA measurement zones 15 from each other and from the touch screen display 30D. The electrically conductive material 15A of the Bio-Impedance Electrical Analysis (BIA) measurement zones 15 may be coupled to the top surface 11A while leaving an electrically insulating region 18 to separate the Bio-Impedance Electrical Analysis (BIA) measurement zones 15 from the top surface 11A that is integrated with the touch screen 30D.

As perhaps best shown in FIG. 13 and in some embodiments, the apparatus 100A may be held in the hands of the user 200. The user may contact the electrically conductive material 15A of a first Bio-Impedance Electrical Analysis (BIA) measurement zone 15 with a portion of a firsthand such as a finger, while contacting the electrically conductive material 15A of a second Bio-Impedance Electrical Analysis (BIA) measurement zone 15 with a portion of a second hand such as a finger allowing an electrical current to pass through the body of the user 200 for Bio-Impedance Electrical Analysis (BIA) measurements.

While some preferred materials have been described for some elements that comprise the apparatus, other elements may be made from durable materials such as hard plastics, metal alloys, wood, hard rubbers, carbon fiber, or any other suitable materials including combinations of materials. Additionally, one or more elements may be made from durable and slightly flexible materials such as soft plastics, silicone, soft rubbers, or any other suitable materials including combinations of materials.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

REFERENCES (INCORPORATED HEREIN BY REFERENCE)

U G, Kyle et al. "Single prediction equation for bioelectrical impedance analysis in adults aged 20-94 years." Nutrition. Vol. 17, No. 3, March 2001.

What is claimed is:

1. A touch input biometric apparatus for measuring and communicating biometric data of a user, the apparatus comprising:
   a. a platform having a top surface with a center region and a perimeter region;
   b. a touch screen display integrated into the top surface of the platform and configured to receive touch input from a user through a disturbance in an electrical field, the touch screen display occupying substantially all of the center region of the top surface of the platform;
   c. a first BIA measurement zone surrounding a portion of the touch screen and comprising an electrically conductive material integrated into the perimeter region of the top surface of the platform and configured to transfer an electrical current to a first foot of a user, the first BIA measurement zone positioned along a first distal side of the platform;
   d. a second BIA measurement zone surrounding a portion of the touch screen and comprising an electrically conductive material integrated into the top surface of the perimeter region of the platform, the second BIA measurement zone positioned along a second distal side of the platform and said electrically conductive material electrically coupled to a BIA sensor configured to measure electrical impedance;
   e. the touch screen positioned between both the first BIA measurement zone and the second measurement zone thereby separating the first BIA measurement zone and the second BIA measurement zone; and
   f. a electrically insulating region positioned around a perimeter of the touch screen between the touch screen and the first and second BIA measurement zones thereby electrically insulating the touch screen from the first BIA measurement zone and the second BIA measurement zone.

2. The apparatus of claim 1, wherein the first BIA measurement zone and the second BIA measurement zone are positioned on the top surface of the distal edge of the platform.

3. The apparatus of claim 2, wherein the platform comprises a second electrically insulating region positioned between the electrically conductive material of the first BIA measurement zone and the electrically conductive material of the second BIA measurement zone.

4. The apparatus of claim 1, wherein the touch screen display is between the first BIA measurement zone and second BIA measurement zone and wherein the first BIA measurement zone comprises a C shape with opposing top and bottom sides connected by a side edge and the second BIA measurement zone comprises an inverted C shape with opposing top and bottom sides connected by a side edge.

5. The apparatus of claim 1, wherein the electrically insulating region has a width between 0.1 to 50 mm wide.

6. The apparatus of claim 1, wherein the platform is configured to receive weight from a user and the apparatus further comprises a weight sensor configured to measure the weight of the user and display the weight on the touch screen display.

7. The apparatus of claim 1, wherein the apparatus further comprises a Bluetooth receiver and a Bluetooth transmitter.

8. The apparatus of claim 1, wherein the apparatus comprises a WiFi receiver and a WiFi transmitter.

9. A touch input biometric apparatus for measuring and communicating biometric data of a user, the apparatus comprising:
   a. a platform with a top surface, a first elongate side, a second elongate side opposite to the first elongate side, a third side perpendicular to and connected with the first elongate and the second elongate sides, and a forth side opposite to the third side and perpendicular to and connected with the first and second elongate sides, the platform configured to contact a user;
   b. a touch screen display integrated into a substantial portion of a central region of the top surface of the platform and configured to receive touch input from a user;
   c. a first BIA measurement zone comprising a first electrically conductive material integrated into the top surface of the platform and configured to transfer an electrical current to the skin of a user, the first BIA measurement zone positioned along a portion of the first elongate side, a portion of the second elongate side, and the third side forming a C shape measurement zone;
   d. a second BIA measurement zone comprising a second electrically conductive material integrated into the top surface of the platform configured to contact the skin of the user and configured to receive the electrical current from the first BIA measurement zone that passes through the user, the second BIA measurement zone positioned along a portion of the first elongate side, a portion of the second elongate side, and the forth side forming an inverted C shape measurement zone;
   e. an electrically insulating region, wherein the electrically insulating region extends around a distal edge of the touch screen display between the first and second BIA measurement zones; and
   f. a BIA sensor, wherein the BIA sensor is electrically coupled to the first and second BIA measurement zones and configured to measure the electrical impedance of the user contacting the platform and display an estimation of the user's percent body fat on the touch screen display.

10. The apparatus of claim 9, wherein the first electrically conductive material of the first BIA measurement zone is electrically coupled to a first electrode and the electrically conductive material of the second BIA measurement zone is electrically coupled to a second electrode.

11. The apparatus of claim 10, further comprising an electrically insulating region positioned between the first BIA measurement zone and the second BIA measurement zone.

12. The apparatus of claim 11, further comprising an electrically insulating region positioned between the touch screen and each of the first and second BIA measurement zones.

13. The apparatus of claim 9, further comprising a radio configured to wirelessly receive and transmit data to an electronic device.

14. The apparatus of claim 13, wherein the radio comprises a Bluetooth receiver and a Bluetooth transmitter.

15. The apparatus of claim 13, wherein the radio comprises a WiFi receiver and a WiFi transmitter.

* * * * *